US011077218B1

(12) United States Patent
Gagnon et al.

(10) Patent No.: US 11,077,218 B1
(45) Date of Patent: Aug. 3, 2021

(54) PAYMENT TERMINAL SANITIZING DEVICE

(71) Applicants: Patrick Gagnon, Garland, TX (US); Grace Rose Gagnon, Garland, TX (US)

(72) Inventors: Patrick Gagnon, Garland, TX (US); Grace Rose Gagnon, Garland, TX (US)

(*) Notice: Subject to any disclaimer, the term of this patent is extended or adjusted under 35 U.S.C. 154(b) by 0 days.

(21) Appl. No.: 17/208,311

(22) Filed: Mar. 22, 2021

Related U.S. Application Data

(60) Provisional application No. 62/993,942, filed on Mar. 24, 2020.

(51) Int. Cl.
A61L 2/10 (2006.01)
A61L 2/24 (2006.01)
G07F 7/00 (2006.01)

(52) U.S. Cl.
CPC ............ A61L 2/10 (2013.01); G07F 7/005 (2013.01); A61L 2202/11 (2013.01); A61L 2202/20 (2013.01)

(58) Field of Classification Search
CPC .......... A61L 2/10; A61L 2/24; A61L 2202/14; A61L 2202/11; A61L 2202/121; A61L 2202/122; A61L 2202/15; A61L 2202/16; A61L 2202/20; A61L 2/00; A61L 2/0088; A61L 2/18; A61L 2/202; A61L 2/22; A61L 2/28; A61L 9/00; A61L 9/20; G01N 30/30; G01N 2030/027; G01N 2030/3038

USPC ....... 250/504 R, 492.2, 455.11, 454.11, 288, 250/282

See application file for complete search history.

(56) References Cited

U.S. PATENT DOCUMENTS

| 4,710,634 | A | * | 12/1987 | Brookes | .................... A61L 2/10 250/455.11 |
| 6,458,331 | B1 | * | 10/2002 | Roberts | .................... A61L 2/10 422/186.3 |
| 8,297,435 | B2 | | 10/2012 | Lathem | |
| 9,233,179 | B2 | | 1/2016 | Ranta et al. | |
| 9,242,018 | B2 | | 1/2016 | Cole et al. | |
| 9,974,875 | B2 | * | 5/2018 | Davis | .......................... A61L 2/24 |
| 10,850,184 | B1 | * | 12/2020 | Colvin | ...................... A61L 9/20 |
| 2009/0101814 | A1 | * | 4/2009 | Amirav | ................ H01J 49/0431 250/288 |

(Continued)

Primary Examiner — David A Vanore
(74) Attorney, Agent, or Firm — Boudwin Intellectual Property; Daniel Boudwin

(57) ABSTRACT

A payment terminal sanitizing device includes a housing having a base member configured to removably secure to a payment terminal. The base member includes tabs and slots that engage corresponding tabs and slots on the payment terminal. A top cover is removably secured to the base member. The sides of the top cover and base member curve outwardly to form an interior volume between the top cover and base portion. The interior volume includes a plurality of brackets configured to support individual UV lights that are positioned on opposing sides of the interior of the housing. The UV lights are operably connected to a power source, such as a wall outlet, for example. The UV lights are oriented such that they illuminate or irradiate the input mechanisms of the payment terminal, in order to prevent the spread of germs between individual users of the payment terminal.

16 Claims, 5 Drawing Sheets

(56) References Cited

U.S. PATENT DOCUMENTS

| | | | |
|---|---|---|---|
| 2010/0127189 A1* | 5/2010 | Boyarsky | A61L 2/24 |
| | | | 250/492.2 |
| 2011/0049031 A1* | 3/2011 | Cappiello | G01N 30/32 |
| | | | 210/198.2 |
| 2013/0045133 A1 | 2/2013 | Maguire | |
| 2013/0062534 A1* | 3/2013 | Cole | A61N 5/0624 |
| | | | 250/454.11 |
| 2015/0090903 A1* | 4/2015 | Cole | A61L 2/10 |
| | | | 250/492.1 |
| 2017/0035923 A1* | 2/2017 | Yanke | A61L 2/10 |
| 2017/0184552 A1* | 6/2017 | Guzzonato | H01J 49/0468 |
| 2017/0333582 A1* | 11/2017 | Davis | A61L 2/10 |
| 2018/0339075 A1* | 11/2018 | Kennedy | E05B 1/0069 |
| 2020/0300822 A1* | 9/2020 | Cappiello | G01N 30/30 |

* cited by examiner

US 11,077,218 B1

PAYMENT TERMINAL SANITIZING DEVICE

CROSS REFERENCE TO RELATED APPLICATIONS

This application claims the benefit of U.S. Provisional Patent Application No. 62/993,942 filed on Mar. 24, 2020. The above identified patent application is herein incorporated by reference in its entirety to provide continuity of disclosure.

BACKGROUND OF THE INVENTION

The present invention relates to an ultraviolet (UV) light sanitizing device. More specifically, the present invention provides a sanitizing device configured to secure to an existing payment terminal, such that UV light is directed at the input buttons and other contact surfaces of the payment terminal, in order to sanitize the surfaces to prevent the spread of viruses, bacteria, and other germs.

Most places of business that sell goods and services to the general public have at least one electronic payment terminal. These payment terminals typically include an electronic display, a card reader, and one or more input mechanisms, such as buttons or touchscreens, for example. Many individuals contact these input mechanisms as they use the card reader to complete their transactions. This leads to the spread of viruses, bacteria, and other germs that are present on the input mechanisms' surfaces. The payment terminal may be cleaned at some point, but it is rarely cleaned between each individual use, so germs are still transmitted. Some places of business attempt to mitigate the spread of germs by providing a dispenser filled with liquid sanitizer, intending that customers sanitize their hands before and after using the payment terminal. However, many customers forgo using the sanitizer liquid and germs are spread regardless. In order to address these concerns, the present invention provides a sanitizing device that attaches to a payment terminal and sanitizes the contact surfaces of the payment terminal with UV light.

Devices existing in the known art that include UV lights for sanitizing common contact surfaces. However, these devices have several drawbacks. Some of these devices are handheld and must be manually directed by the user, which can be ineffective and time consuming. Other devices provide generic UV systems that irradiate a general area. However, these are less effective because their lighting is often directed to cover a larger area and not as concentrated in a single area where germs congregate.

In light of the sanitizing devices and methods disclosed in the known art, it is submitted that the present invention substantially diverges in design elements from the prior art and consequently it is clear that there is a need in the art for an improvement to existing sanitizing devices, particularly with regards to sanitizing payment terminal contact surfaces. In this regard the present invention substantially fulfills these needs by providing a UV sanitizing device specifically designed to sanitize payment terminal contact surfaces with UV radiation.

SUMMARY OF THE INVENTION

In view of the foregoing disadvantages inherent in the known types of sanitizing devices now present in the prior art, the present invention provides a new UV sanitizing device wherein the same can be utilized for providing convenience for the user when sanitizing payment terminal contact surfaces to reduce the spread of germs.

The payment terminal sanitizing device generally includes a housing having a base member configured to removably secure to a payment terminal. A top cover portion is removably secured to the base member. The sides of the top cover and base portion curve outwardly to form a recessed interior volume along the interior perimeter between the top cover and base member. The recessed interior volume includes a plurality of bracket members configured to support individual UV lights that are positioned on opposing sides of the housing for maximum coverage. The UV lights are operably connected to a power source, such as a wall outlet, for example. The UV lights are positioned such that they illuminate or irradiate the input mechanisms of the payment terminal, such as the buttons or touchscreen. In this way, the payment terminal buttons and other contact areas are sanitized by the UV radiation, preventing the spread of germs between individual users of the payment terminal.

One object of the present invention is to provide a payment terminal sanitizing device that can be easily attached to an existing payment terminal.

Another object of the present invention is to provide a payment terminal sanitizing device that continuously applies UV radiation to the common contact surfaces of the payment terminal to effectively prevent the spread of germs.

A further object of the present invention is to provide a payment terminal sanitizing device that may be readily fabricated from materials that permit relative economy and are commensurate with durability.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
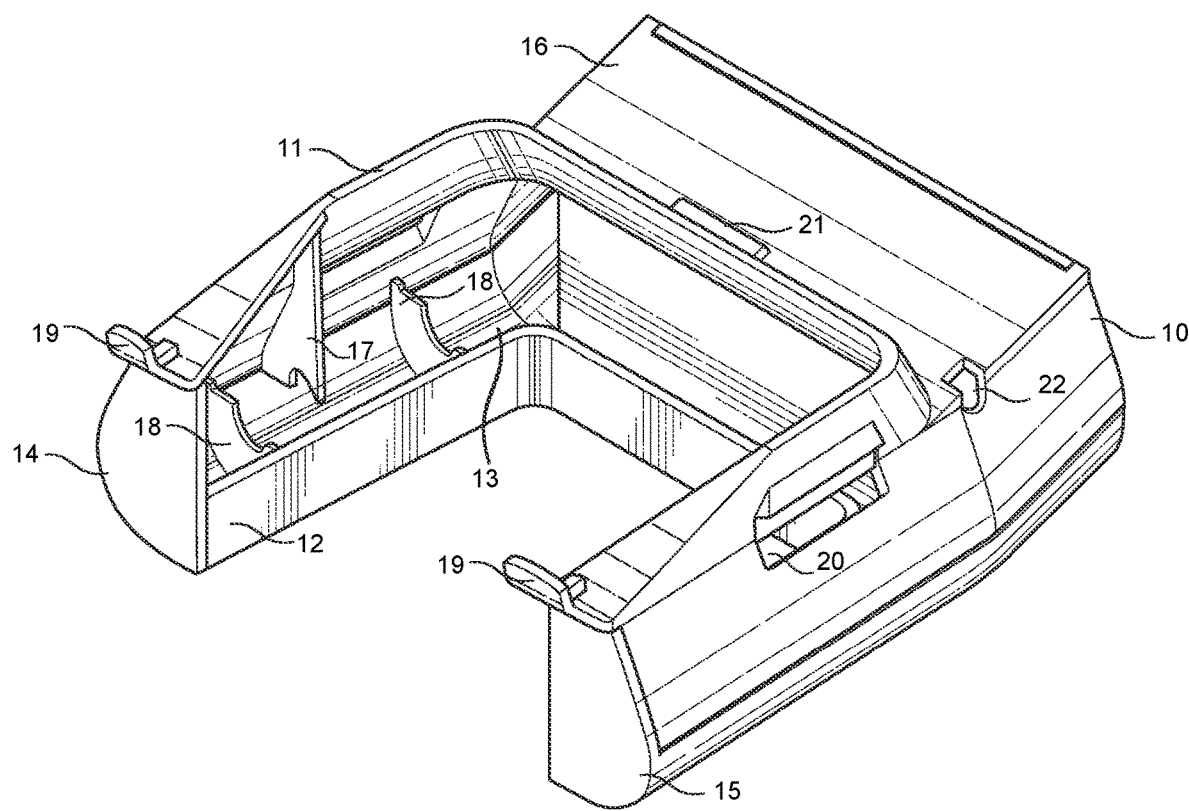
FIG. 1 shows a perspective view of an embodiment of the payment terminal sanitizing device.

Reference is made herein to the attached drawings. Like reference numerals are used throughout the drawings to depict like or similar elements of the payment terminal sanitizing system. For the purposes of presenting a brief and clear description of the present invention, the preferred embodiment will be discussed as used for providing a payment terminal sanitizing system that applies UV light to payment terminal contact surfaces in order to prevent germs from spreading between individuals users of the payment terminal. The figures are intended for representative purposes only and should not be considered to be limiting in any respect.

Figure 4:
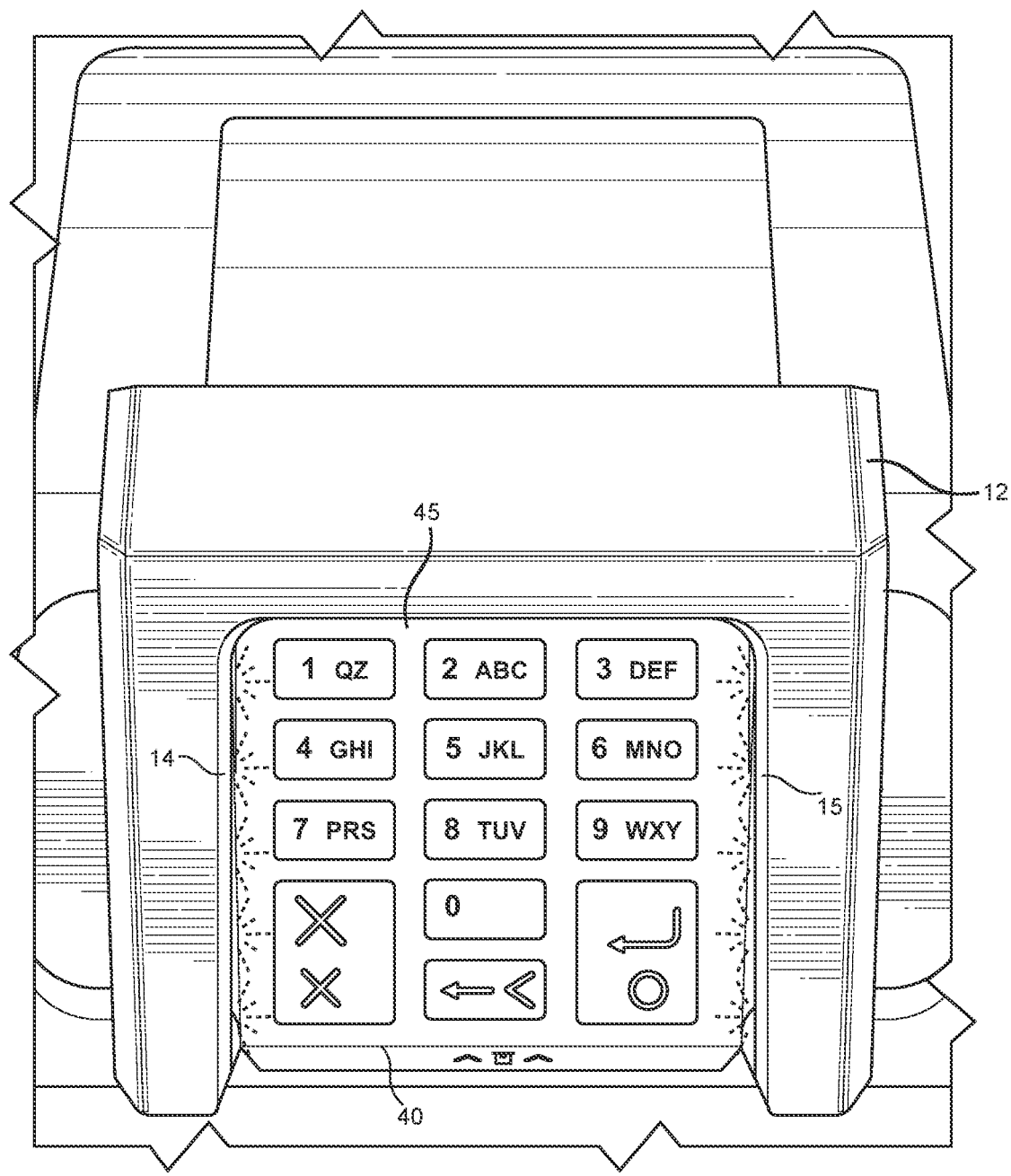
FIG. 4 shows a perspective view of an embodiment of the payment terminal sanitizing device attached to a payment terminal.

Referring now to FIG. 1, there is shown a perspective view of an embodiment of the payment terminal sanitizing device. The device generally includes a housing 10 comprising a top cover 12 removably secured to a base member 11. The device is shown here in an inverted orientation, with the top cover 12 beneath the base member 11, for better visibility. The housing shape includes an upper end 16 having a pair of side portions 14, 15 extending downwardly from opposing sides of the upper end portion 16. This defines a central opening which provides access to a payment terminal input mechanism, as shown in FIG. 4.

The base member 11 may include multiple tabs, slots, and other fasteners for removable engagement with a payment terminal housing. In one example, a payment terminal's existing top cover or shroud can be removed to expose various mounting tabs and slots that correspond with the base member 11 tabs and slots. In the shown embodiment, the base member includes a pair of angled tabs 19 that extend from the side portions 14, 15 of the housing, which include pegs that removably engage apertures on the payment terminal housing. The base member 11 also includes a pair of slots 20 disposed on the side portions 14, 15, and an upper tab 21 that is disposed on the upper end 16 of the housing. The tabs and slots can be configured for use with different types of payment terminals. In other words, other embodiments may include different configurations of tabs and slots for removably securing the device to an existing payment terminal without the need for modifying the structure of the payment terminal.

The base member 11 and the top cover 12 define an interior volume 13 in which UV lights are supported. The UV lights are supported via a plurality of brackets positioned within the interior volume 13. In some embodiments, the interior surfaces of the base member 11 and the top cover 12 include reflective materials, such as an attached layer of aluminum foil for example, which helps to direct the UV radiation toward the payment terminal for more effective sanitization. In the shown embodiment, the plurality of brackets includes a single lower bracket 17 attached to the base member 11 and a pair of upper brackets 18 attached to the top cover 12 and positioned on opposing sides of the lower bracket 17. This arrangement of the brackets provides a cradle that frictionally secures the UV light in place when the top cover 12 and base member 11 are secured to one another. The brackets are also partially flexible, so a user can change out UV lights as needed.

Figure 2:
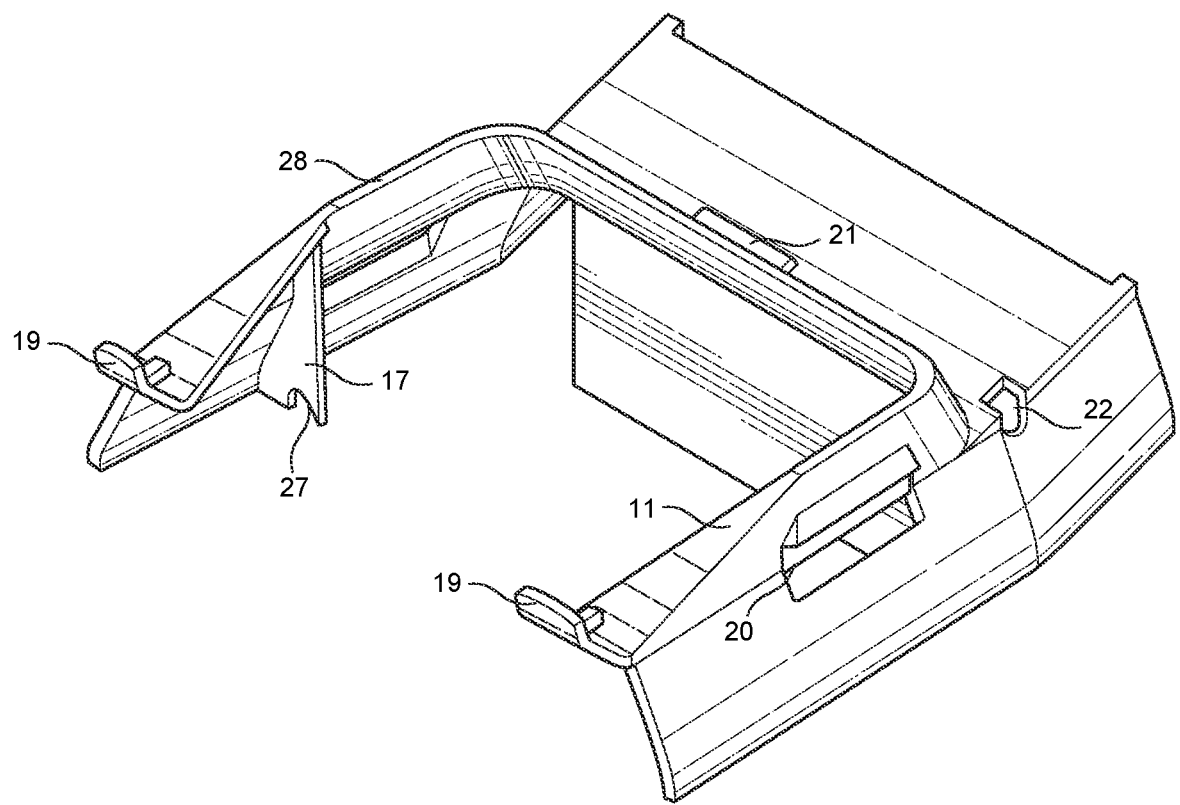
FIG. 2 shows a perspective view of the base member of an embodiment of the payment terminal sanitizing device.
Figure 3:
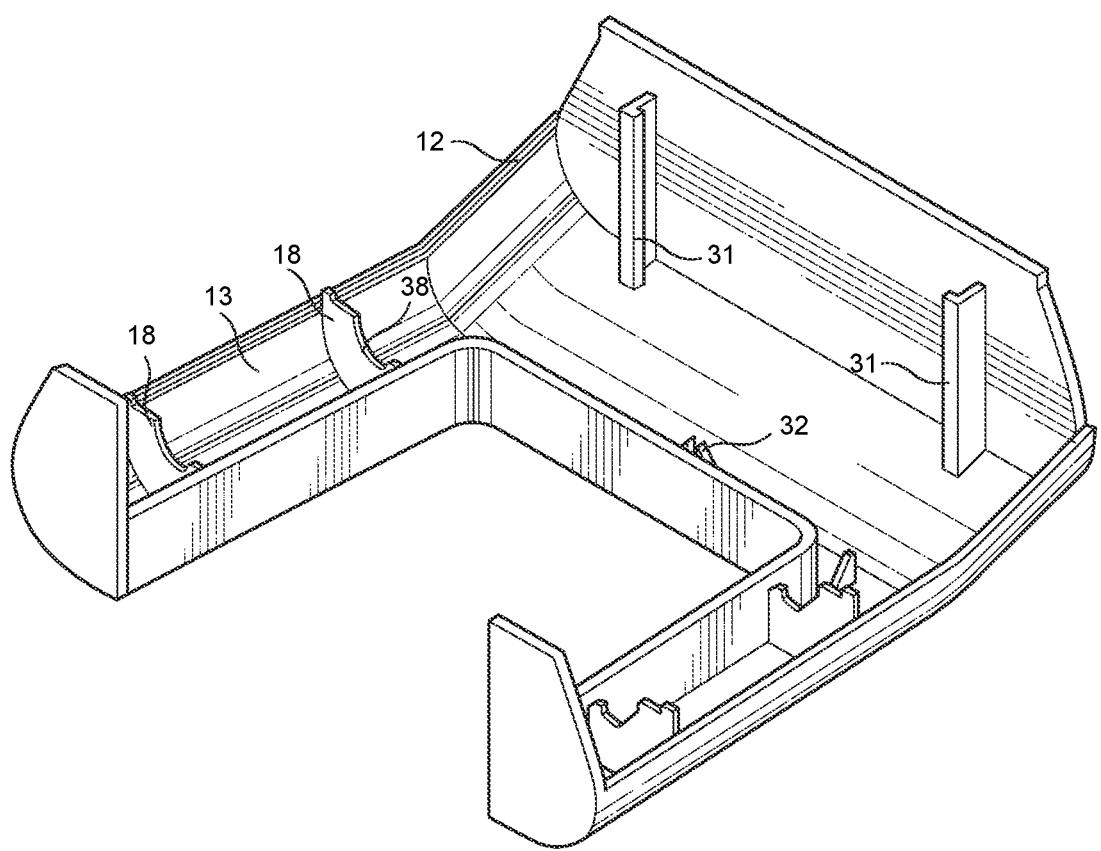
FIG. 3 shows a perspective view of the top cover of an embodiment of the payment terminal sanitizing device.

Referring now to FIGS. 2 and 3, there is shown a perspective view of the base portion of an embodiment of the payment terminal sanitizing device and a perspective view of the top cover of an embodiment of the payment terminal sanitizing device, respectively. In some embodiments, the top cover 12 and base member 11 are removably secured to one another via friction fit, while other embodiments can use various fasteners, and other embodiments can include a singular housing with integral top and bottom portions. As shown in FIG. 2, the base member bracket 17 includes a curved interior edge 27, which is configured to contour to an exterior surface of the UV light. Similarly, as shown in FIG. 3, the top cover brackets 18 can include a similarly curved interior edge 38 for effectively securing the UV lights in place.

Referring now to FIG. 4, there is shown a perspective view of an embodiment of the payment terminal sanitizing device attached to a payment terminal. When attached to a payment terminal 40, the housing defines an open central area that exposes the input mechanisms 45 of the payment terminal. The shown example includes buttons and a lower card reader, but the present invention can be utilized with different types of payment terminals having different types of input mechanisms, including touchscreens, for example. The UV lights are positioned within each of the side portions 14, 15 such that they irradiate the input mechanisms 45 of the payment terminal. Further, the side portions 14, 15 of the top cover 12 extend inwardly to cover the upper part of the UV lights, which prevents excess UV radiation from being directed toward the face of the user of the payment terminal.

Figure 5:
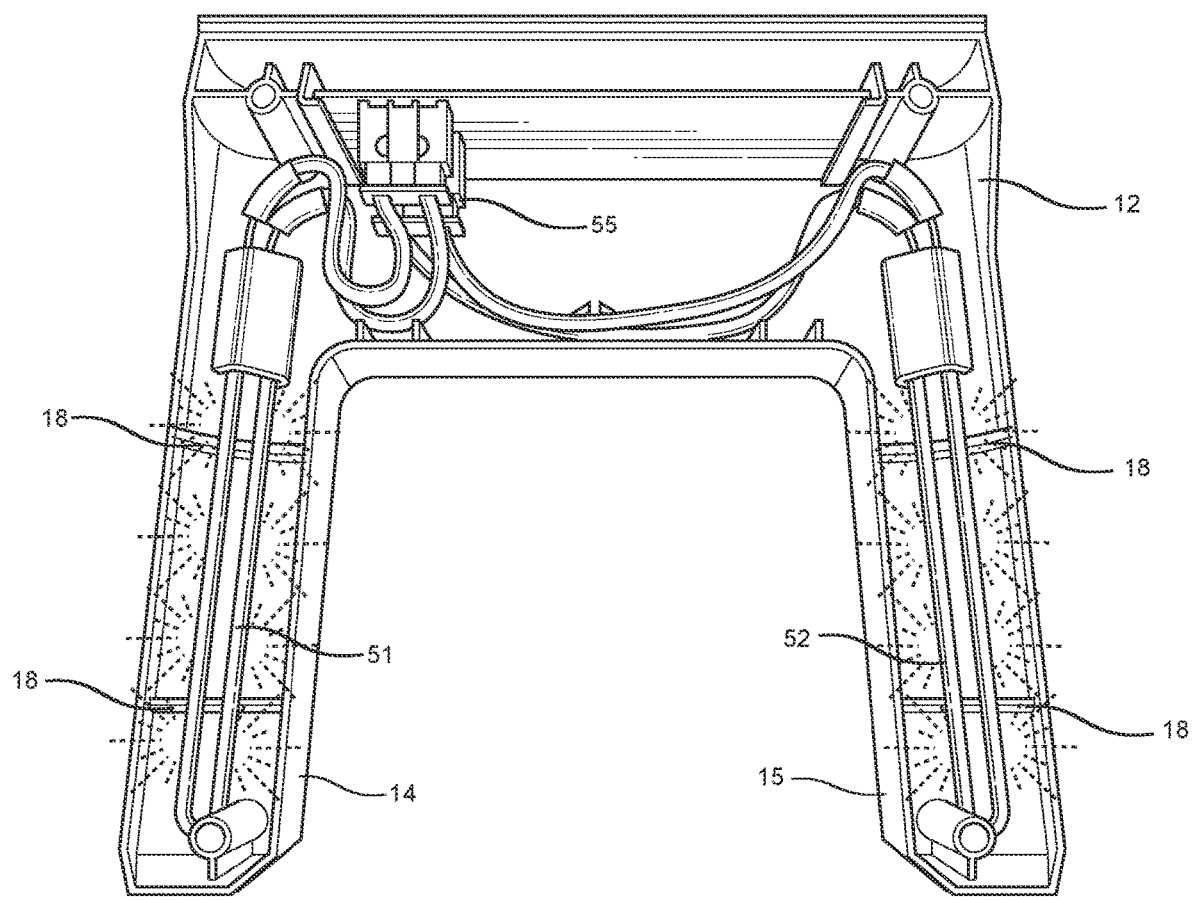
FIG. 5 shows a perspective view of the interior of an embodiment of the terminal sanitizing device, with the base member removed to show an example configuration of the UV lights.

Referring now to FIG. 5, there is shown a perspective view of the interior of an embodiment of the terminal sanitizing device, with the base portion removed to show an example configuration of the UV lights. In the shown embodiment, the device includes a pair of UV lights 51, 52 secured in respective side portions 14, 15 of the housing. The bracket or cradle members 18 of the top cover 12 help to support and secure the UV lights 51, 52 in position. In the shown embodiment, the UV lights are ultraviolet light bulbs, but other embodiments may include UV light emitting diodes. In one embodiment, the UV lights 51, 52 are configured to emit UVC light having a wavelength between the range of one hundred nanometers and two-hundred eighty nanometers, which is one of the most effective wavelength ranges for germ eradication.

The UV lights 51, 52 are shown connecting to a power inverter 55, which is configured to convert standard 120V AC electricity from a standard pronged wall outlet plug (not shown) to 12V DC electricity for powering the UV lights 51, 52. However, other power sources may be utilized. For example, some embodiments may include rechargeable batteries. In such embodiments, the device may include charging ports or other means for charging the rechargeable batteries. In the shown embodiment, the connection to the power source for the UV lights 51, 52 causes the UV lights 51, 52 to illuminate, such that the contact surfaces of the payment terminal are continuously irradiated, providing for maximum effectiveness of the UV lights 51, 52. In other embodiments, the device can include sensors that can activate or deactivate the UV lights in response to some external sensed condition.

In operation, the present invention can be easily installed on an existing payment terminal that lacks sanitizing means. For example, the device can include tabs and slots that correspond to similar tabs and slots on the housing of the payment terminal. When attached, the UV lights are positioned such that the most common contact surface, the input mechanism, is surrounded on either side from above by the UV lights. In this way, when the UV lights are activated, they continuously irradiate the surface of the payment terminal input mechanism. This helps to constantly kill germs, including new germs that may be transferred to the payment terminal by new users of the payment terminal. The constant irradiation provided by the UV lights sanitizes the payment terminal's input mechanism, such that individual users of the payment terminal no longer spread germs amongst themselves due to contact with the payment terminal.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A payment terminal sanitizing device, comprising:
a housing comprising a top cover removably secured to a base member;
the base member removably securable to a payment terminal;
the top cover and base member defining an interior volume;
a plurality of brackets positioned within the interior volume, the plurality of brackets configured to support a UV light within the interior volume, the plurality of brackets comprising at least one cradle member attached to the top cover and at least one cradle member attached to the bottom cover, such that the UV light is supported between the cradle members;
wherein the UV light is oriented to irradiate an input mechanism of the payment terminal when the base member is removably secured thereto.

2. The payment terminal sanitizing device of claim 1, wherein the UV light is an ultraviolet light bulb.

3. The payment terminal sanitizing device of claim 1, wherein the UV light is an ultraviolet light emitting diode.

4. The payment terminal sanitizing device of claim 1, wherein the UV light is operably connected to a power source.

5. The payment terminal sanitizing device of claim 1, further comprising a power inverter configured to receive electrical power via a connection to a wall outlet.

6. The payment terminal sanitizing device of claim 1, wherein the UV light comprises a UVC light configured to emit light having a wavelength between the range of one hundred nanometers and two-hundred eighty nanometers.

7. The payment terminal sanitizing device of claim 1, whereby the housing defines a central opening that permits access to the input mechanism of the payment terminal.

8. The payment terminal sanitizing device of claim 1, wherein each bracket of the plurality of brackets includes a curved interior edge that contours to an exterior surface of the UV light.

9. A payment terminal sanitizing device, comprising:
a housing comprising a top cover removably secured to a base member, wherein the housing further comprises an upper end portion and a pair of side portions extending downwardly from opposing sides of the upper end portion;
the base member removably securable to a payment terminal;
the top cover and base member defining an interior volume;
a pair of UV lights comprising a UV light secured within each side portion of the housing;
a plurality of brackets positioned within the interior volume, the plurality of brackets configured to support a UV light within the interior volume, the plurality of brackets comprising at least one cradle member attached to the top cover and at least one cradle member attached to the bottom cover, such that the UV light is supported between the cradle members;
wherein the UV light is oriented to irradiate an input mechanism of the payment terminal when the base portion is removably secured thereto.

10. The payment terminal sanitizing device of claim 9, wherein each UV light is an ultraviolet light bulb.

11. The payment terminal sanitizing device of claim 9, wherein each UV light is an ultraviolet light emitting diode.

12. The payment terminal sanitizing device of claim 9, wherein each UV light is operably connected to a power source.

13. The payment terminal sanitizing device of claim 9, further comprising a power inverter configured to receive electrical power via a connection to a wall outlet a power inverter configured to receive electrical power via a connection to a wall outlet.

14. The payment terminal sanitizing device of claim 9, wherein each UV light comprises a UVC light configured to emit light having a wavelength between the range of one hundred nanometers and two-hundred eighty nanometers.

15. The payment terminal sanitizing device of claim 9, wherein the pair of side portions of the housing extend inwardly to cover above each UV light of the pair of UV lights, whereby the housing defines a central opening that permits access to the input mechanism of the payment terminal.

16. The payment terminal sanitizing device of claim 9, wherein each bracket includes a curved interior edge that contours to an exterior surface of each UV light.

* * * * *